(12) United States Patent
Killinger et al.

(10) Patent No.: US 7,812,946 B1
(45) Date of Patent: Oct. 12, 2010

(54) DEEP-UV LED AND LASER FLUORESCENCE APPARATUS FOR MONITORING WATER QUALITY

(75) Inventors: Dennis K. Killinger, Temple Terrace, FL (US); Anna Sharikova, Tampa, FL (US); Vasanthi Sivaprakasam, Washington, DC (US)

(73) Assignee: University of South Florida, Tampa, FL (US)

( * ) Notice: Subject to any disclaimer, the term of this patent is extended or adjusted under 35 U.S.C. 154(b) by 338 days.

(21) Appl. No.: 11/926,196

(22) Filed: Oct. 29, 2007

Related U.S. Application Data

(60) Provisional application No. 60/863,249, filed on Oct. 27, 2006.

(51) Int. Cl.
*G01J 3/30* (2006.01)
(52) U.S. Cl. ..................................... 356/317
(58) Field of Classification Search ....................... None
See application file for complete search history.

(56) References Cited

U.S. PATENT DOCUMENTS

| | | | | |
|---|---|---|---|---|
| 6,475,803 | B1 * | 11/2002 | Ueno et al. | 436/166 |
| 6,541,272 | B1 * | 4/2003 | Mitra | 436/178 |

OTHER PUBLICATIONS

Killinger, Dennis et al., Water Monitoring with Laser Fluorescence, OPN Jan. 2006, p. 35-39, www.osa-opn.org.
Pulse of the Planet Web site on fresh water usage: www.pulseplanet.com/archive/Jan00/2057.html, Jan. 2000.
Clescerl, L.S., Greenberg, A.E., Eaton, A.D., Standard Methods for Examination of Water and Wastewater, Am. Public Health Assoc., 20th Ed., 1999.
Coble, P.G., Characterization of Marine and Terrsestrial DOM in Seawater Using Excitation-Emission Matrix Spectroscopy, Marine Chemistry 51, p. 325-46, 1996.
Global Trends 2015, National Intelligence Council Report, #0441-015-00211-2, Dec. 2000.
Goodson, A. et al., Survey of Bisphenyl-A and Bisphenol-F in Canned Foods, Food Add. Contam. 19, 796-802, 2002.

(Continued)

*Primary Examiner*—Tu T Nguyen
(74) *Attorney, Agent, or Firm*—Ronald E. Smith; Smith & Hopen, P.A.

(57) ABSTRACT

A method for detecting trace levels of dissolved organic compounds and leached plastic compounds in drinking water includes the steps of employing deep ultraviolet light-emitting diode induced fluorescence at sensitivity levels of several parts per trillion in real time so that a more compact and inexpensive excitation source, relative to a deep UV laser-induced fluorescence, for fluorescence detection of dissolved organic compounds in water is provided. The deep UV light-emitting diode is operated at an excitation near 265 nm and the laser induced fluorescence is detected at an emission near 450 nm to 500 nm for the dissolved organic compounds and near 310 nm for leached plastic compounds. Optical absorption filters and optical bandpass filters are employed to reduce out-of-band light emitting diode emissions and to eliminate second order optical interference signals for the detection of a fluorescence signal near 450 nm to near 500 nm. The system can measure water contained within a quartz optical cell, within bottled water containers, or in a flowing stream of water.

12 Claims, 20 Drawing Sheets
(18 of 20 Drawing Sheet(s) Filed in Color)

Diagram of LEDIF-LIF setup

OTHER PUBLICATIONS

Sivaprakasam, V. and Killinger, D.K., Effects of Polarization and Geometrical Factors on Quantitative Laser-Induced Fluorescence-to-Ramen Intensity Ratios of Water Samples and a New Calibration Technique, J. Opt. Soc. Am. B 20, 1980 (2003).

Sivaprakasam, V. and Killinger, D.K., Tunable Ultraviolet Laser-Induced Fluorescence detection of Trace Plastics and Dissolved Organic Compounds in Water, Applied Optics, 42, 6739, 2003.

Sivaprakasam, V. et al., Development and Initial Calibration of a Portable Laser Induced Fluorescence System Used for In Situ Measurements of Trace Plastics and Organics in Seawater and the Gulf of Mexico, Applied Optics, 42, 6747, 2003.

Maclusky, N.J. et al., The Environmental Estrogen Bisphenol-A Inhibits Estradiol-Induced Hippocampal Synaptogenesis, Environmental Health Perspectives, 113, 647-679, 2005.

* cited by examiner

Samples obtained over a five-day research cruise through the Gulf of Mexico. The increased emission due to DOCs near 450 nm was correlated to outflow form river plumes into the Gulf.

COMPARISON OF EXCITATION BY UV LED AND LASER

We compared water fluorescence induced by a JDS Uniphase microchip laser with that of two UV-TOP LEDs from Sensor Electronic Technology, Inc. The fluorescence emission was detected by the Ocean Optics spectrometer USB2000.

| Laser characteristics | | LED characteristics | 265 nm LED | 320 nm LED |
|---|---|---|---|---|
| Wavelength | 266 nm | Forward voltage | 5.5 V | |
| Pulse width | 0.4 ns | Forward current | 10 mA | |
| Pulse energy | 0.4 µJ | | | |
| Repetition rate | 8 kHz | Power at 10 mA | 0.11 mW | 0.09 mW |
| Average power | 3 mW | Actual peak wavelength | 268 nm | 319 nm |
| | | Spectrum half-width | 12 nm | |

Fig. 13

DEEP-UV LED AND LASER FLUORESCENCE APPARATUS FOR MONITORING WATER QUALITY

CROSS REFERENCE TO RELATED APPLICATIONS

This application claims priority to U.S. Provisional Patent Application 60/863,249, entitled, "Deep-UV Led and Laser Fluorescence Apparatus for Monitoring Water Quality", filed Oct. 27, 2006, the contents of which are herein incorporated by reference.

STATEMENT OF GOVERNMENT INTEREST

This invention was made with U.S. government support under grant No. W911NF-05-1-0431 awarded by the U.S. Army Research Office, and grant No. N00014-04-1-0555 awarded by the U.S. Office of Naval Research. The U.S. government has certain rights in the invention.

BACKGROUND OF THE INVENTION

1. Field of the Invention

This invention relates to the monitoring of water quality and the detection of trace dissolved organic compounds, leached plasticizers, and/or carbon (DOCs) in water and drinking water.

2. Description of the Prior Art

Most approaches for monitoring water quality in water processing plants are based on "wet" chemistry techniques that require the addition of other chemicals to water samples. Many use gas chromatography or liquid chromatography followed by laser fluorescence detection in a reagent capillary tube, while others use reagents that change pH, color, or other physical characteristics depending upon the concentration of selected or trace species. Although useful in the lab, these techniques work less well in the field, where reagents are difficult to replace and harsh conditions may degrade them.

Earlier laser-induced fluorescence (LIF) studies of water have used either blue-green (513.5 nm) argon ion lasers or doubled (535 nm) Nd:YAG lasers for excitation, as well as staining reagents for improving the contrast of detected organisms. Studies that have relied on natural or auto-fluorescence from water have generally not been as successful as those that have used fluorescent dyes. This is perhaps because blue-green wavelengths do not sufficiently separate between the emission spectral peaks due to trace organics versus excitation or interfering background spectra.

As a result, few previous LIF studies have drawn on the natural fluorescence of trace species in the water. The novel system therefore employs a deep-UV laser source near 220 nm-300 nm for excitation to overcome some of the limitations of the natural fluorescence approach. The resultant fluorescence emission from the organics is well separated from the excitation wavelength.

There is a need for a reagentless, deep UV (220 nm-300 nm) laser-induced-fluorescence (LIF) system for detecting contaminates and potentially harmful substances in bottled and processed water and the ocean.

It is known that expensive laser-based fluorescence detection of dissolved organic compounds in drinking water is feasible. Previous work by the inventors has shown that laser induced fluorescence can be used for the detection of trace DOCs and leached plasticizers (such as Bisphenol-A) in water and that different drinking water samples from different bottled water manufacturers show significant different levels of DOCs and/or plasticizers. Such prior art work appears in several research publications such as: (1) Tunable ultraviolet laser-induced fluorescence detection of trace plastics and dissolved organic compounds in water, Vasanthi Sivaprakasam and Dennis K. Killinger, Applied Optics 42, 6739 (2003), (2) Development and initial calibration of a portable laser induced fluorescence system used for in situ measurements of trace plastics and organics in seawater and the Gulf of Mexico, Vasanthi Sivaprakasam, Robert Shannon, Caiyan Luo, Paula G. Coble, Jennifer Boehme, and Dennis K. Killinger, Applied Optics 42, 6747 (2003), and (3) Water Monitoring with Laser Fluorescence, Dennis Killinger and Vasanthi Sivaprakasam, Invited Review, OSA Optics and Photonics News, p 35, January 2006

The 266 nm UV laser used for excitation in these published prior art studies by the authors and inventors cost $10,000. Accordingly, there is a need for a low cost, compact LED to replace the known expensive lasers.

Currently, no real time or reagentless laser-induced-fluorescence systems have been authorized for use by water treatment plants. However, for the past several years, some water agencies have been testing a selected range of UV absorption and fluorescence water monitoring instruments. One such device is a UV-visible (200 nm-750 nm) absorption instrument from S-CAN in Austria that can detect small changes in the optical absorption properties of water.

Another fluorescence-based test is used to monitor water for the e-coli bacteria. This involves growing a culture obtained from a water sample, using a fluorescence dye or stain, and counting the organisms by either visual microscopes or laser readers. Fluorescence is also used in liquid chromatography laser-induced fluorescence, or LC-LIF, a technique in which a capillary tube is used to separate the chemical species and a laser reads the separated column.

However, in view of the art considered as a whole at the time the present invention was made, it was not obvious to those of ordinary skill in this art how the identified needs could be met.

SUMMARY OF INVENTION

The long-standing but heretofore unfulfilled need for a compact, less expensive UV LED-based laser-induced fluorescence instrument to detect and monitor dissolved organic compounds and/or carbon in drinking water in real time is now met by a new, useful, and nonobvious invention that detects deep-UV (near 266 nm) laser and deep-UV LED excited fluorescence emission (near 450 to 500 nm) of the DOCs in the water.

The novel method for detecting trace levels of dissolved organic compounds in drinking water includes the steps of employing a deep ultraviolet (UV) light-emitting diode laser-induced fluorescence at sensitivity levels of several parts per trillion in real time. This provides a more compact and inexpensive excitation source, relative to a deep UV laser-induced fluorescence, for laser-induced fluorescence detection of dissolved organic compounds in water. The cost of the deep-UV LED (near 265 nm) is about $100.00, and consumes much less power and is more compact than the deep-UV 266 nm laser (cost of $10,000).

The deep UV light-emitting diode is preferably operated at an excitation near 266 nm and the laser-induced fluorescence is detected at an emission near 450 nm to 500 nm. Excitation in the UV up to wavelengths near 320 nm can be used for excitation, but optical filtering is less selective and the sensitivity is less than that obtained using wavelengths near 265 nm or less.

Optical absorption filters and optical bandpass filters are employed to reduce out-of-band light emitting diode (LED) emissions and to eliminate second order optical interference signals for the detection of a fluorescence signal near 450 nm to near 500 nm.

A modulated continuous wave LED excitation source is employed to produce detection sensitivity within a factor of twenty (20) to thirty (30) times relative to a pulsed (8.6 KHz) 266 nm laser source.

A pulsed (about 10 KHz PRF) LED source and a gated (100 ns) detection system is used to provide gated noise rejection of the fluorescence signal to obtain increased sensitivity and reduced background noise because the fluorescence lifetime of the dissolved organic compounds in water is about 50 ns.

Modulated continuous wave LEDs using a lock-in amplifier signal processing and pulsed LEDs using gated boxcar integrators are employed to optimize the dissolved organic compound fluorescence signals and improve the signal-to-noise ratio.

Grating spectrometers and silicon detectors arrays, and/or sets of optical filters in a sequential wheel arrangement with photomultiplier detectors are employed to detect the fluorescence emission.

The novel system has a sensitivity of about a few parts per trillion, which is several orders of magnitude better than conventional spectrofluorometers. It has detected the presence of plastic resins and dissolved organic compounds in bottled drinking water, monitored real time changes in DOCs in drinking water processed by reverse osmosis, and has been used to track DOCs and river plumes in the Gulf of Mexico.

Conventional spectrofluorometers use Xenon lamps and excitation filtering spectrometers to produce the UV excitation beam, but their beam intensity is three to nine orders of magnitude less intense than that available with a laser or LED source.

Pulsed atomic emission lamps in the deep-UV (such as a low-pressure mercury lamp) and optical narrow-line filters may be used for the deep-UV excitation source in the fluorescence system. Such lamps are less intense than LEDs and lasers by several orders of magnitude, but provide sufficient excitation power if the DOC fluorescing concentrations is extremely large.

BRIEF DESCRIPTION OF THE DRAWINGS

The patent or application file contains at least one drawing executed in color. Copies of this patent or patent application publication with color drawings will be provided by the Office upon request and payment of the necessary fee. For a fuller understanding of the invention, reference should be made to the following detailed description, taken in connection with the accompanying drawings, in which:

FIG. 13 is a table showing a comparison of excitation by UV, LED, and laser;

DETAILED DESCRIPTION OF THE PREFERRED EMBODIMENT

Conventional methods of water analysis can achieve a high degree of sensitivity necessary for water quality monitoring, but they often require special sample preparation, additional reagents or chemicals, and often are not conducted in real time or on-line.

Deep ultraviolet (UV) laser-induced fluorescence (LIF) is effective for the detection of trace levels of dissolved organic compounds (DOCS) in water at the parts per billion (ppb) to parts per trillion (ppt) detection level. The instrument used to perform the steps of this invention is a laboratory-developed pulsed laser-induced fluorescence system. Said instrument is different from conventional, commercially-available fluorescence spectrofluorometers in that such spectrofluorometers typically include a continuous wave (CW) xenon emission lamp, a grating spectrometer for excitation, and a spectrometer for emission analysis. The novel system uses a chopped (about 200 Hz) CW excitation source, so the signal processing involves detection of the chopped fluorescence signal. Such detection usually employs a lock-in amplifier. However, the use of a high-PRF (pulse-repetition-frequency) pulsed laser source for excitation allows use of a gated boxcar-integrator to detect the fluorescence emission, and gains several orders of magnitude in signal-to-noise.

The data in FIGS. 1-8 is a disclosure of prior art involved in the laser-induced-fluorescence (LIF) detection of dissolved organic compounds in drinking water using a high power, expensive UV laser source.

Figure 7:
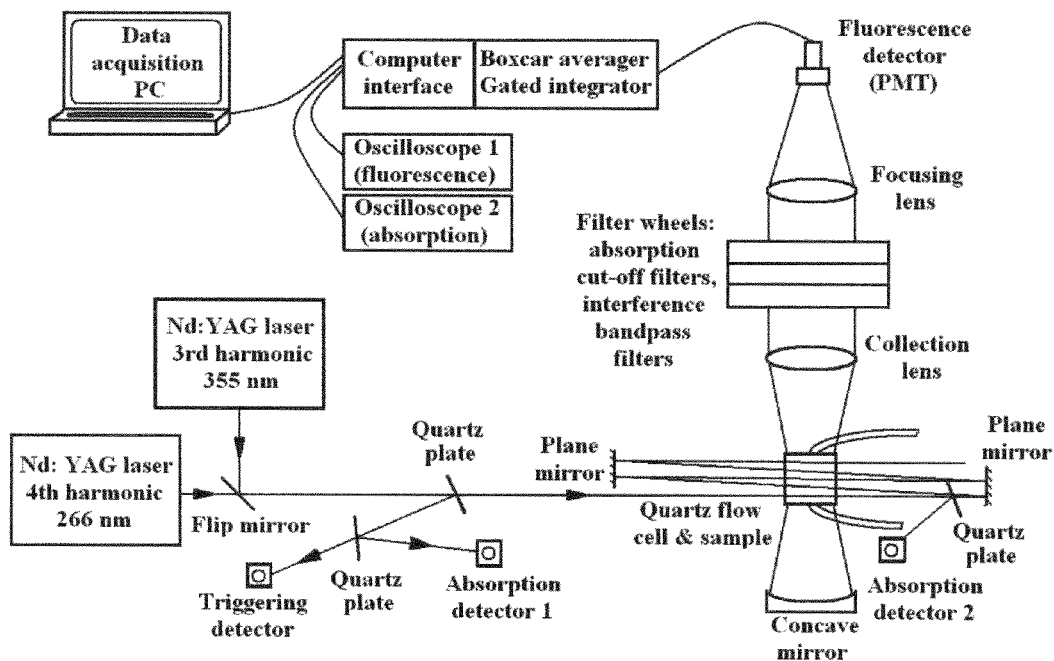
FIG. 7 is a prior art diagram of a portable LIF system.
Figure 8:
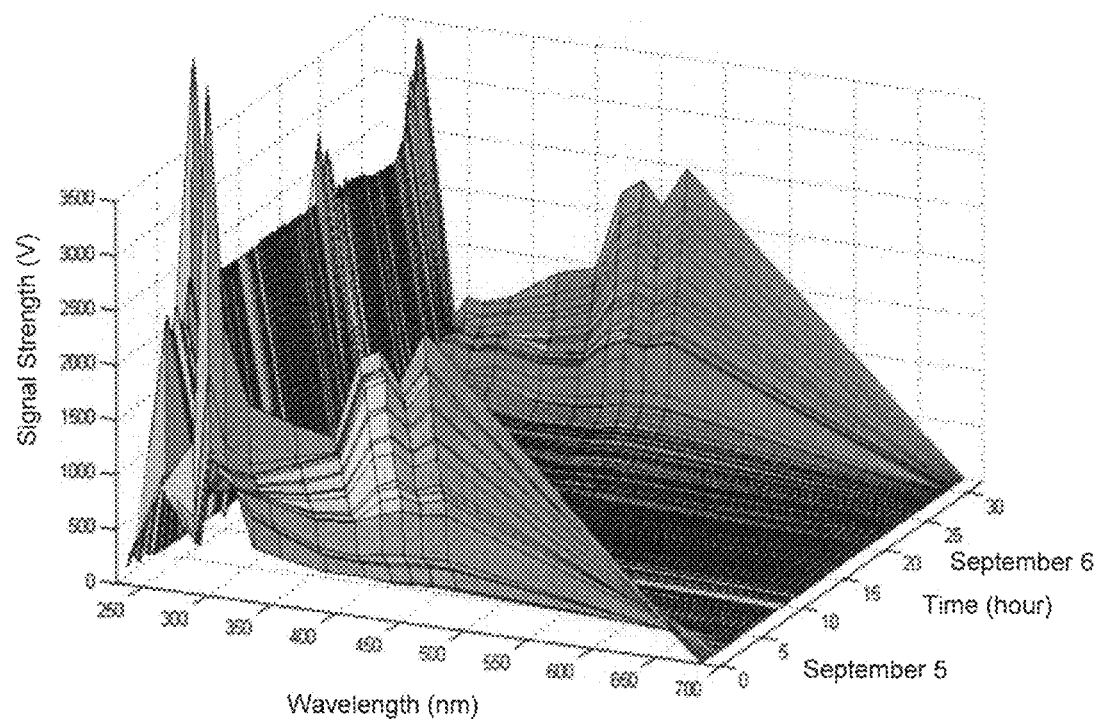
FIG. 8 is a prior art graphical depiction of the fluorescence of Gulf of Mexico water.

The LIF system light sources are two interchangeable high pulse-repetition frequency (8.6 kHz) UV lasers, 266 nm and 355 nm, illuminating a quartz cell with a flowing water sample. The optics include focusing lenses and filter wheels with cut-off and optical interference filters selecting different wavelength ranges. The fluorescence signal detected by a photo multiplier tube (PMT) is sent to a gated integrator and boxcar averager. The system is integrated with a notebook computer and provides data in real time. FIG. 7 diagrammatically depicts a portable LIF system.

Figure 1:
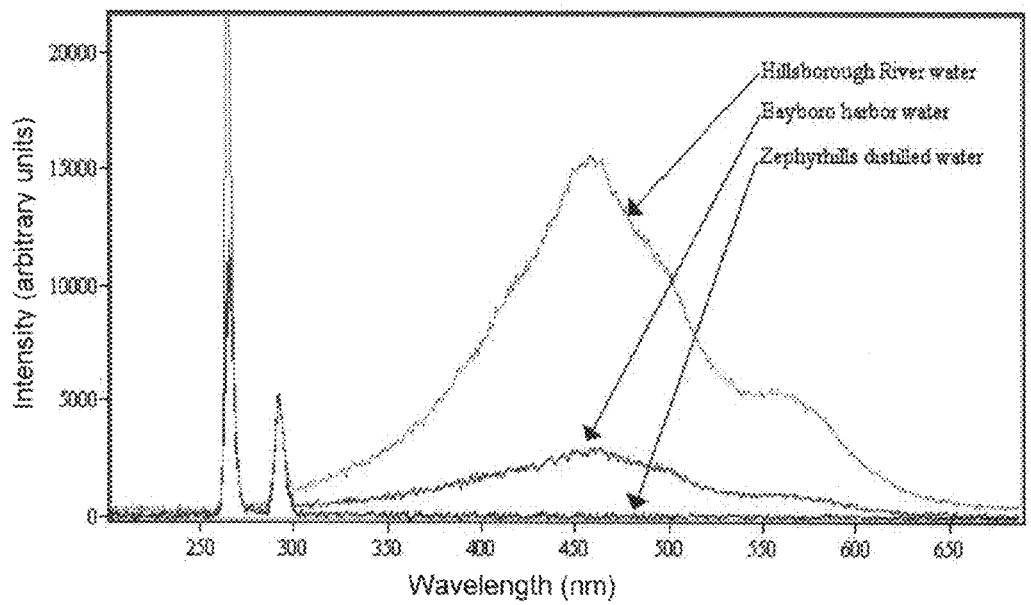
FIG. 1 is a prior art graphical depiction of fluorescence emission from natural water samples obtained using 266 nm laser excitation.
Figure 2:
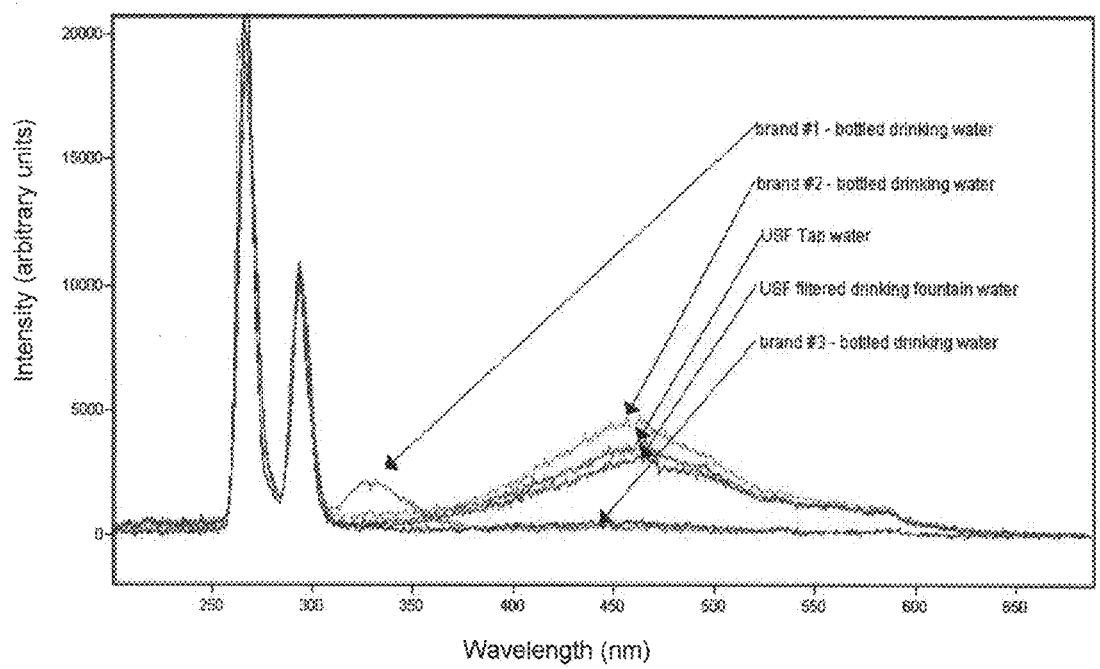
FIG. 2 is a prior art graphical depiction of fluorescence emission from bottled water.
Figure 3:
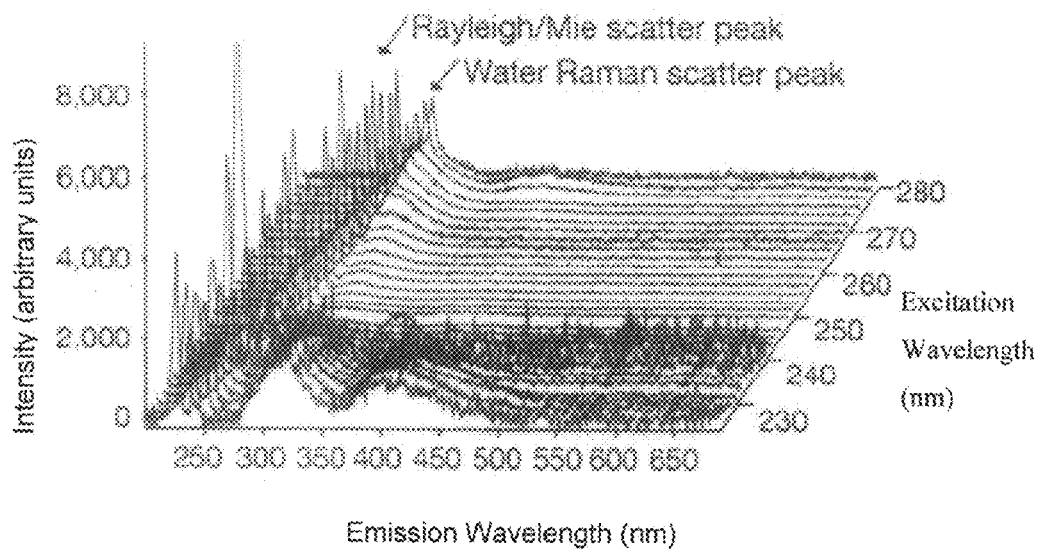
FIG. 3 is a prior art graphical depiction of an excitation-emission-matrix spectrum of bisphenol-A.
Figure 4:
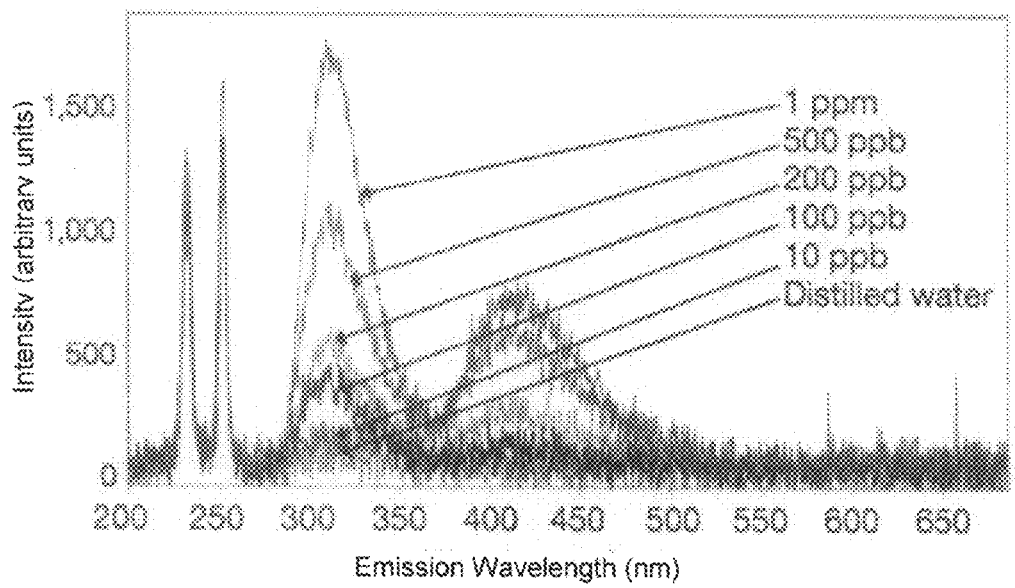
FIG. 4 is a prior art graphical depiction of an LIF spectrum from various concentrations of bisphenol-A.
Figure 5:
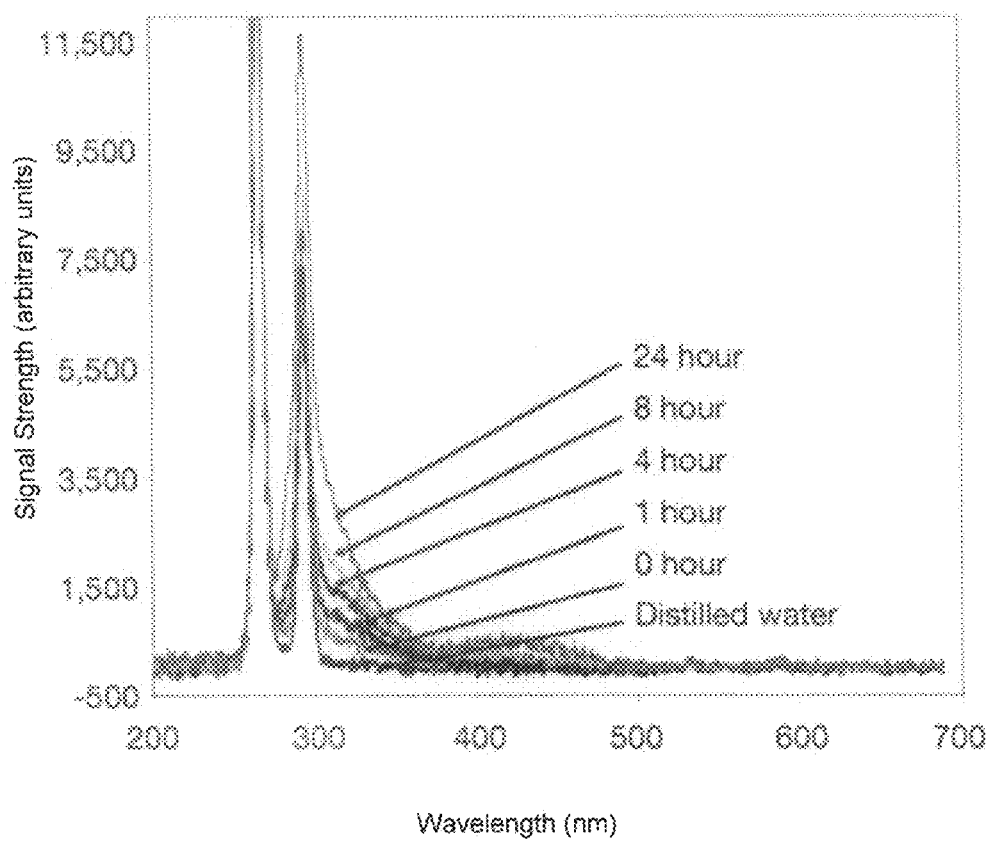
FIG. 5 is a prior art graphical depiction of LIF emissions for resins leached from a plastic container.
Figure 6:
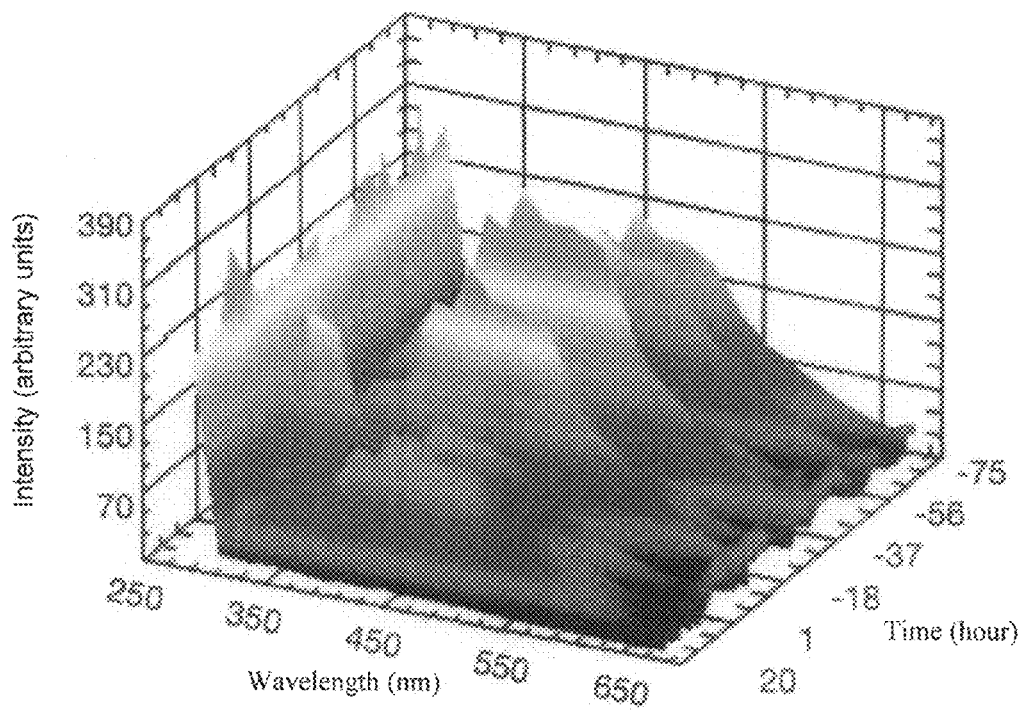
FIG. 6 is a prior art graphical depiction of LIF spectral data from the Gulf of Mexico.

The LIF system is used to record fluorescent spectra of different water samples, such as distilled (FIG. 1), tap (FIG. 2), and river water (FIG. 1). Substantial differences in spectra are observed between different brands of distilled bottled water. The river samples display large fluorescence peaks near 450-500 nm corresponding to the fluorescence of DOCs. The spectra of water processed by a reverse osmosis (RO) water purification unit has also been recorded. The unique fluorescence from plastic compounds (Bisphenol-A) near 310 nm were detected and shown in FIG. 4

The signal-to-noise ratio (S/N) of conventional spectrofluorometers may be improved by replacing the conventional CW or chopped xenon light sources with a high pulse-repetition-frequency (PRF) laser. The novel method employs high PRF-gated boxcar signal processing instead of conventional analog lock-in amplification. The spatial coherence of the excitation laser beam is also harnessed to allow for multi-passing of the beam within the fluorescence cell.

By gating the boxcar processor only around the short (1 to 20 ns) laser and emitted fluorescence pulse, detector noise between laser pulses is rejected. This technique is viable when the fluorescence lifetime of the emitting species such as the DOCs and plastic resins is short (10 to 20 ns). Assuming equal average laser or optical excitation intensity, the improvement "I" is on the order of the square root of the ratio of the laser pulse period, $T_{laser}$, and the fluorescence lifetime or boxcar gate time, $T_{gate}$, or $$I=(T_{laser}/T_{gate})^{1/2}$$

For example, in the case of a microchip laser operating at a PRF of 8.6 KHz ($T_{laser}$ of 0.1116 ms) and a boxcar gate width of $T_{gate}$ of 50 ns, the improvement expected is close to 50.

The signal-to-noise ratio may also be improved by conducting high-speed pulse averaging of more than 8,600 pulses in one second; however, such an improvement applies equally to the CW or high-PRE pulsed laser case.

Several LIF systems which differed with regard to their laser tunability and spectroscopic detection techniques were considered. The decision of which to use was based on whether a laboratory tunable spectral survey was to be studied or a fixed wavelength field LIF instrument was to be deployed.

For tunable excitation and laboratory spectroscopic studies, either (1) a large tripled Nd:YAG pumped optical parametric oscillator (doubled) to produce 10 to 30 mJ/pulse, 20 Hz PRF, tunable excitation from 220 nm to 350 nm; or (2) a smaller nitrogen laser pumped doubled dye laser with 1 µJ/pulse, 20 Hz and tunable from 220 nm to 321 nm may be used.

The larger laser is used for initial spectroscopic work. However, a larger laser will photobleach many trace species unless its power is attenuated. Accordingly, a tunable doubled dye laser is relied upon for most of the tunable spectroscopic survey work disclosed herein.

A field-deployable portable LIF unit, diagrammatically depicted in FIG. 7, includes a fixed wavelength 266-nm microchip laser (1 µJ/pulse, PRF 836 kHz) and a 355-nm microchip laser that produces a factor of about one hundred (100) times the average power of the doubled dye laser. In all cases, the output of the lasers is focused into a 1-cm-wide quartz fluorescence cell through which water samples flow.

The emitted fluorescence is collected with a lens, which is analyzed with a spectrometer and cooled CCD detector or PMT, or spectrally sorted by up to twenty-one (21) optical bandpass filters and detected by a PMT. The S/N of these configurations as well as that of a more moderate sensitivity/micro-spectrometer using quinine sulfate as a fluorescence standard were compared.

With the compact spectrometer as a baseline, the improvement was ×80 for the spectrometer CCD system and ×500 for the optical bandpass filter/PMT system.

The tunable laser system is used to measure the excitation emission matrix (EEM) spectra of DOCs in water. The analysis shows that excitation around 245 to 260 nm is near the absorption peak of the DOCs.

The 266-nm laser source and spectrometer/CCD detection system is used to obtain the fluorescence from various sources of natural water and a number of bottled drinking and distilled waters. In one analysis, depicted in FIG. 1, fluorescence was measured from the Hillsborough River, Tampa Bay harbor water and clean distilled water (Zephyrhills® brand). In another, tap water from the University of South Florida was measured, along with three different brands of commercial bottled drinking water.

The emission spectrum from the natural water showed the attenuated Rayleigh-scattered light at 266 nm, a sharp peak near 290 nm from the Raman water scatter line, and a peak near 450 nm from the DOCs in the water. The signal from the DOCs in the river water was very high because said river has a considerable amount of dissolved organics (tannins) from oak tree leaves.

The analysis of the bottled drinking water showed that two brands had almost no DOC levels, while another brand and the tap water had higher levels.

The prior art includes a plastic resin found to leach from underwater mines and plastic compounds into water. The resin is bisphenol-A, based on mass spectrometry studies. Human endocrine studies have also suggested that bisphenol-A leached from plastic containers and cans may be penetrating the environment and affecting human growth and development.

Along this line of study, we conducted extensive EEM spectral measurements by tuning the doubled dye laser from 220 nm to 340 nm When the laser was tuned from 220 nm to 280 nm, the peak emission on an EEM spectra was near 330 and, with a smaller peak near 400 nm at very short wavelengths and rebuilding at the longer wavelengths, near 260 to 280 nm However, the fluorescence merges with the water Raman line at the longer wavelengths; this is why it is sometimes better to go to a very short wavelength that can be easily distinguished from that of a fluorescence line.

Extensive LIF studies with bisphenol-A established a detection sensitivity of a few hundred parts-per-trillion. On the measured spectrum for different concentrations of bisphenol-A, the primary peak near 310 nm is from bisphenol-A, while the secondary peak near 410 nm has been attributed to salicylic acid—one of the components that results from the photo-induced breakdown of bisphenol-A. In the experiments, care was taken in choosing the rubber and plastic tubing for the water flow system. Plastic leached out from a number of soft rubber or plastic tubing (silicone, C-Flex) and led to a fluorescence signature similar to bisphenol-A, i.e., near 310 nm. To minimize this problem, hard PTFE or PFA was used instead. See FIGS. 3 and 4.

Similar plastic-related compounds were observed leaching from everyday plastic containers, utensils and food storage bags. For example, we measured LIF spectra from distilled water placed in a microwavable plastic container, heated in a microwave oven for three (3) minutes to 65 C, and then placed on a table Although the water had cooled to room temperature within fifteen (15) minutes, the leached plastic concentration increased as a function of time over the next twenty-four (24) hours. See FIG. 5.

Further studies showed similar results for water placed in plastic zip-lock bags at room temperature for a twenty-four (24) hour period; this was accelerated if the samples were initially heated.

Turning now to LIF measurements in ocean water, the microchip lasers at 266 nm and 355 nm and the optical bandpass filter/PMT configuration produced the best overall LIF sensitivity and were configured to fit into two portable travel cases. This system was used for research aboard a research cruise vessel along with other wet chemistry and marine science instruments in order to correlate real time LIF data of DOCs and other spectral signatures.

The LIF system was secured to the cabin of the research vessel. Sample lines were connected into the ship's water flow that continuously pulled water from beneath the ship, into a de-bubbler, and out to the various work stations in the science cabin of the ship. Hydrocast water sampling hordes were deployed, i.e., lowered down into the ocean to bring up water samples for the other wet chemistry instruments. The LIF system operated continuously, 24 hours per day, unattended.

A five-day research cruise started in Key West, cruised through several river and effluent currents within the Gulf of Mexico, and ended in Tampa Bay. Plumes of DOCs were readily evident on the spectral analysis, with some coinciding with a plume of red tide detected by other on-board instruments. Fluorescence was observed near 680 nm that is due to the chlorophyll in phytoplankton. We plotted fluorescence over the five days at 450 nm (peak of DOCs) measured for the two excitation wavelengths at 266 nm and 355 nm and also that for the chlorophyll fluorescence near 680 nm The two sets of data were well correlated, although there were deviations in some water masses. See FIG. 6.

Significantly, the LIF system still had a S/N level of about 100 in the clean, blue water that we encountered about thirty (30) to one hundred (100) miles offshore. Due to the increased sensitivity of the LIF system compared to an onboard commercial spectrofluorometer, this was the first time that the US Marine Science group had ever been able to measure fluorescence levels from the DOCs in clean water.

Figure 9:
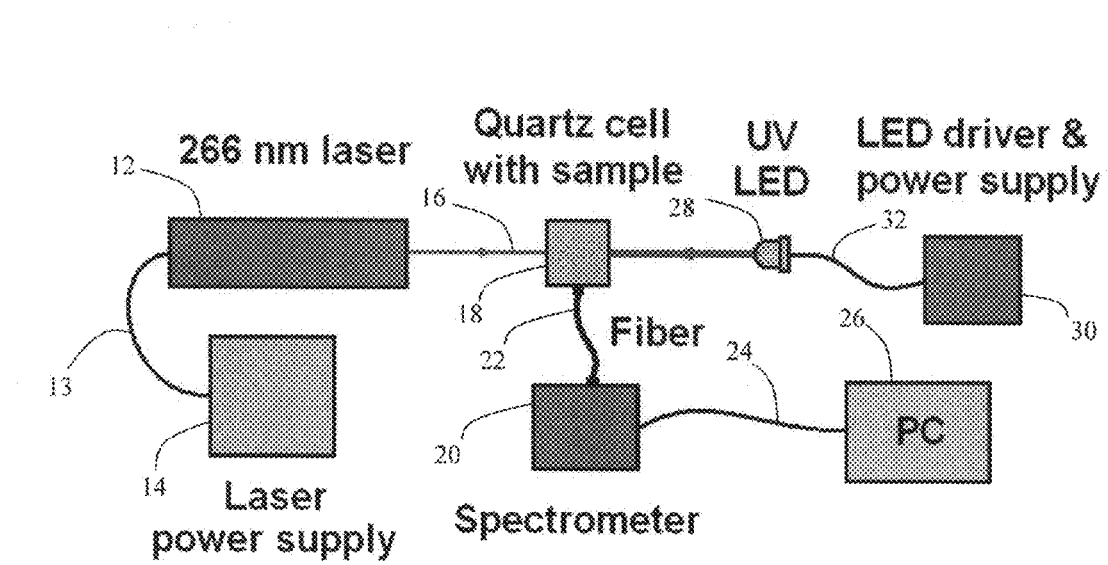
FIG. 9 is a diagram of the novel LED induced-fluorescence (LEDIF)-LIF setup.
Figure 10:
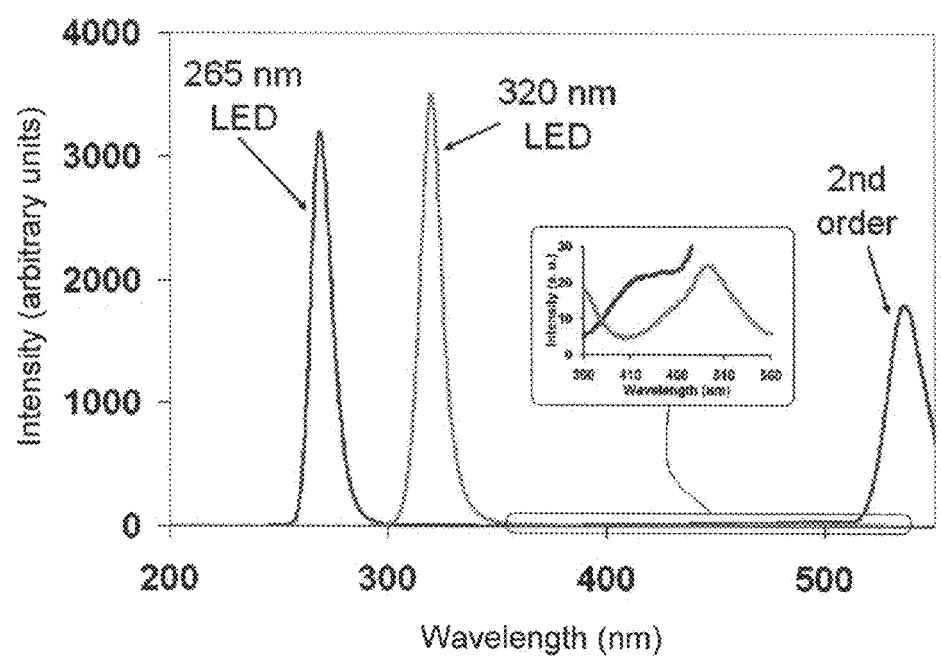
FIG. 10 is a graphical depiction of UV-LED emission spectra.

The data in FIGS. 9-20 is the first disclosure, anywhere in the world, of fluorescence detection of water using a deep-UV LED source. FIG. 9 is a diagrammatic depiction, denoted 10 as a whole, of the experimental setup using a UV LED for excitation and the detection of LED induced fluorescence (LEDIF) emission from water samples contained within a quartz cell. Also depicted in FIG. 9 is excitation using a 266 nm laser source in order to compare the two excitation sources. Said laser source is denoted 12 and its power supply, electrically connected thereto by conductor 13, is denoted 14. Laser source 12 delivers coherent light 16 to quartz cell 18 having a water sample therein. Spectrometer 20 is connected to said quartz cell by optical fiber 22 and said spectrometer is in electrical communication as at 24 with a personal computer 26. The UV LED is denoted 28 and its driver and power supply is denoted 30 and is in electrical communication therewith through conductor 32. The light from the UV LED is denoted 34. The quartz cell 18 can also be any transparent container of water (such as a clear water bottle) that provides optical transmission of the excitation and fluorescence light in that the lens and fiber optics used to direct the light beam into the water can focus the excitation to a focal volume inside the container or cell. The angle between the excitation beam and the collected fluorescence beam can be 90 degrees as shown in FIG. 9, but any angle is feasible including 0 degrees. A flowing stream of water can also be used in place of the quartz cell 18.

UV LEDs (265 nm and 320 nm) have utility as light sources for the novel system. The LEDs are compact, low power devices that make the system cheaper and easily transportable. However, their light output is several orders of magnitude lower than that of lasers, and they have much greater beam divergence. The spectra of both LED light sources are graphically depicted in FIG. 10 and show the out of band emissions near 450 nm from the LEDs. The out-of-band LED emission can interfere with the water fluorescence emission, and requires optical absorption filters to reduce to a negligible level.

It has been found that the spectra of fluorescence emission from the DOCs in water for the laser (266 nm) and the LED (265 nm) excitation are similar.

The power of an LED is approximately one-thirtieth of the average laser power.

The measured LED fluorescence intensity is at least one-twentieth of LIF intensity, and can be increased through judicious use of higher LED power, optical system design, and signal processing Optical filtering is required to reduce out-of-band emission from the UV-LED. Optical filtering is used in the fluorescence collection optical path to reduce the strong excitation optical scatter from interfering with the DOC fluorescence emission. For example, the excitation scatter (Rayleigh and Mie scatter) at 265 nm will be seen in the spectrometer output both at 265 nm and at the second order output of the grating at 2×265 nm=530 nm, which can interfere with the first grating order of the fluorescence emission near 500 nm. An optical absorption filter (such as BK-7 glass) was used to reduce the second order 265 nm to a negligible level.

More particularly, a BK-7 or similar optical absorption glass filter is used in the emission arm of the system to reduce the optical scatter (Rayleigh and Mie scatter of the LED beam in the water) in order to not interfere with the organics fluorescence spectrum at 500 nm and to inhibit the second order scatter of the LED from getting into the spectrometer.

Moreover, the LED output power can be increased to improve the fluorescence signal and the UV-LED can be used in pulsed mode to improve the signal-to-noise ratio.

Figure 11:
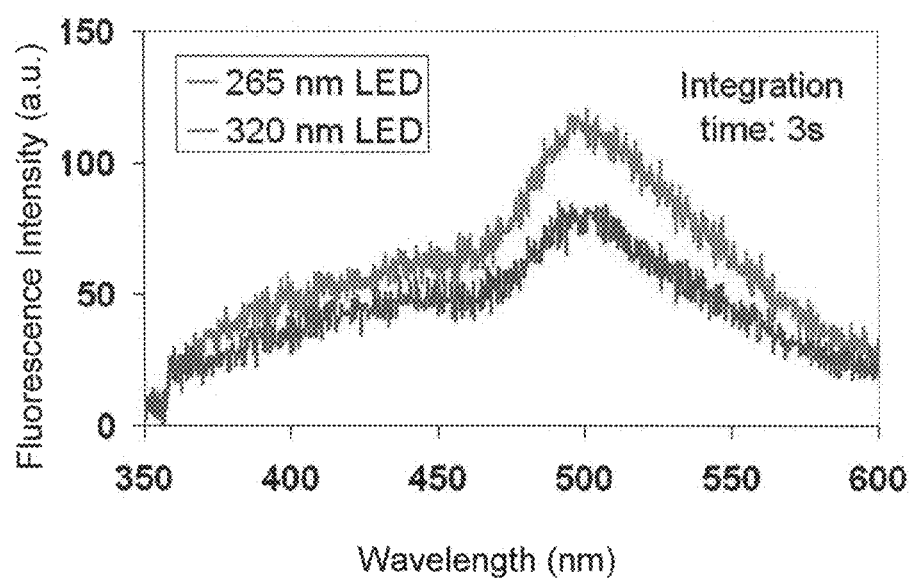
FIG. 11 is a graphical depiction of lake water fluorescence.
Figure 12:
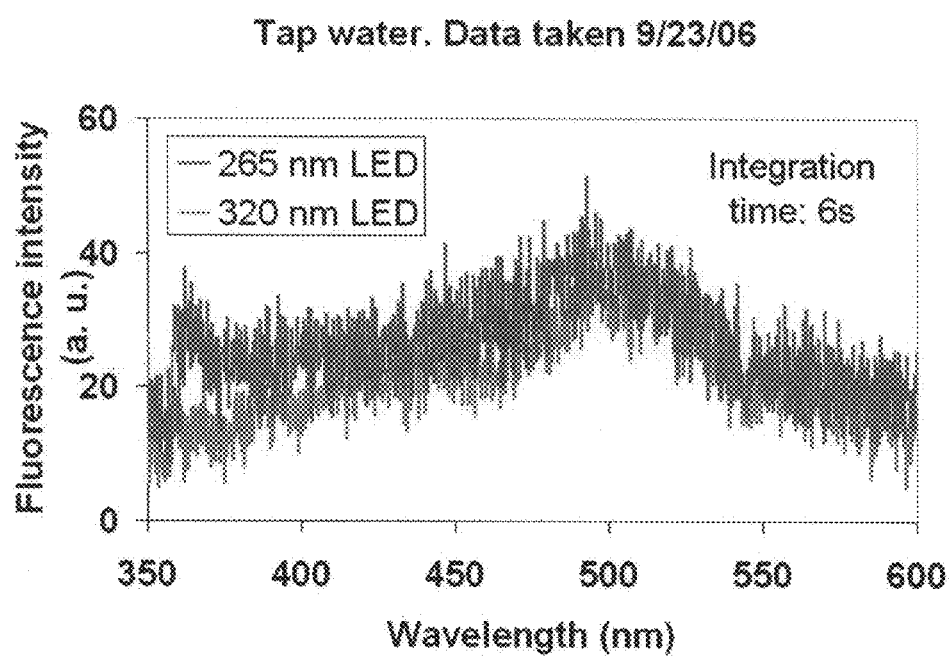
FIG. 12 is a graphical depiction of tap water fluorescence.

Examples of successful detection of water DOCs using the UV LEDs are shown in FIG. 11 for detection of lake water and tap water in FIG. 12.

FIG. 13 depicts some of the technical specifications for the LED sources used. The cost of the LEDs ($100) is much less than the cost of the lasers ($10,000) used in the prior art work, and makes the UV-LED induced fluorescence monitoring of water quality more useful and economical. This substantial cost reduction represents a significant and non-obvious contribution to the art.

Figure 14:
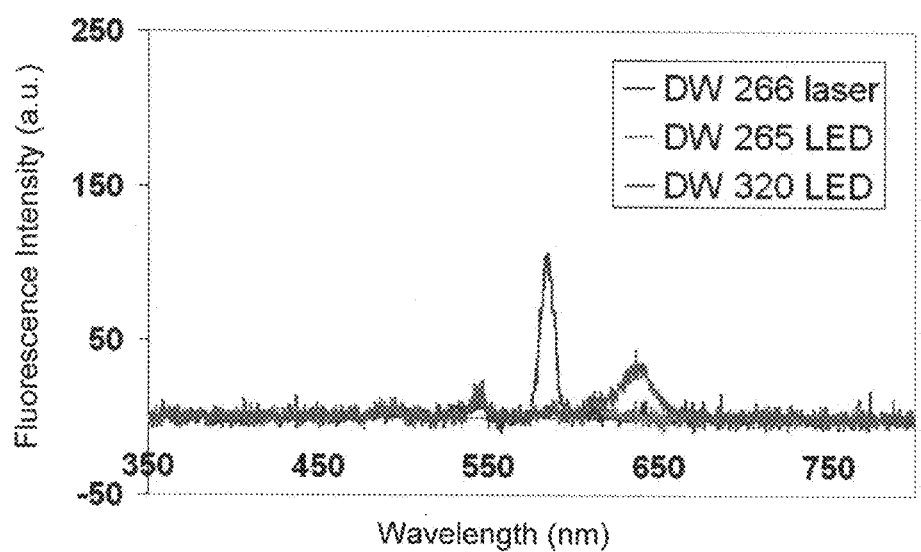
FIG. 14 is a graphical depiction of LED and laser fluorescence of distilled water (without use of optical blocking filters)
Figure 15:
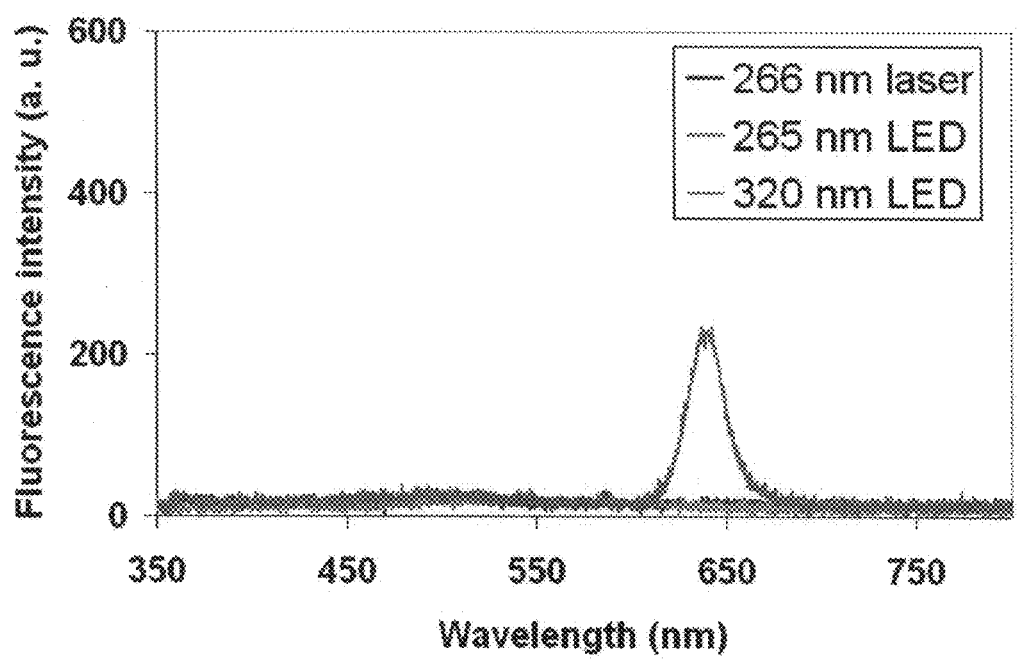
FIG. 15 is a graphical depiction of LED and laser fluorescence of distilled water (with use of optical blocking filters)

FIG. 14 depicts the LED fluorescence signal for distilled water which shows negligible levels of DOCs and fluorescence signal. FIG. 14 depicts the signal without the use of the optical filters to suppress the Rayleigh and Mie scatter and the second order grating signal of the LED beam which acts as interference background. FIG. 15 shows the enhanced fluorescence signal free of interference through the use of the absorption optical filters.

Figure 16:
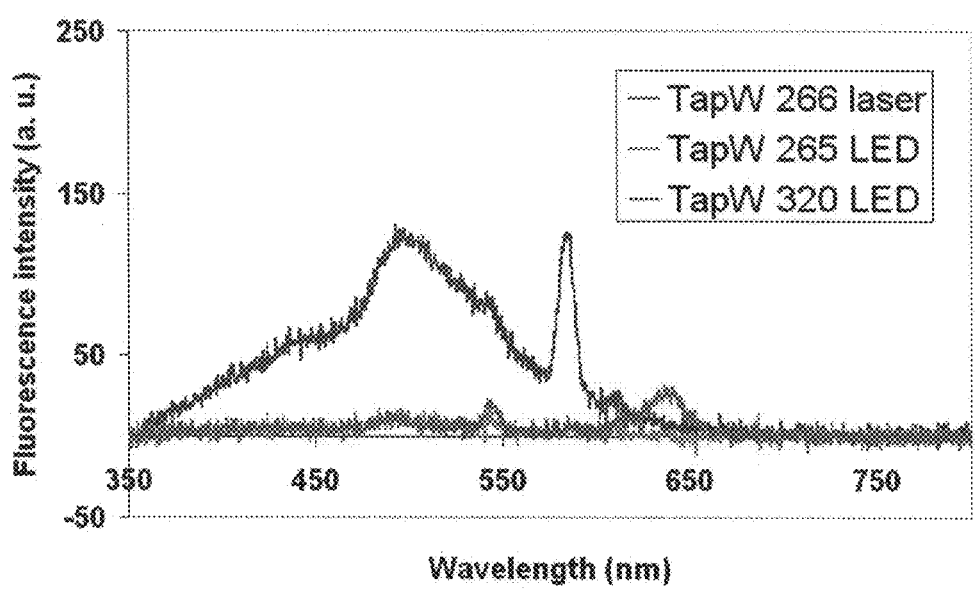
FIG. 16 is a graphical depiction of LED and laser fluorescence of tap water (without use of optical blocking filters)
Figure 17:
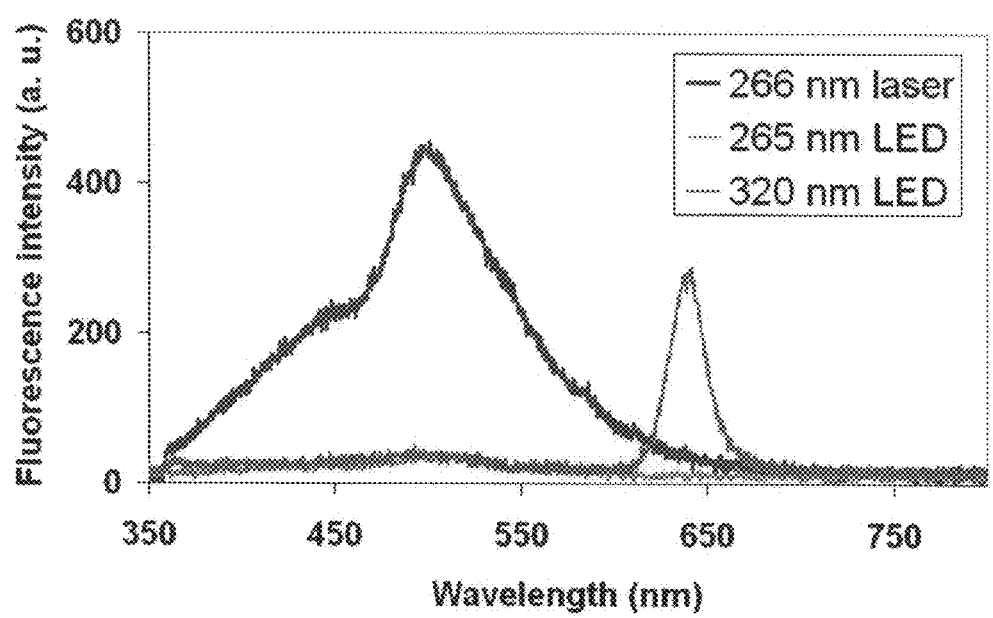
FIG. 17 is a graphical depiction of LED and laser fluorescence of tap water (with use of optical blocking filters)
Figure 18:
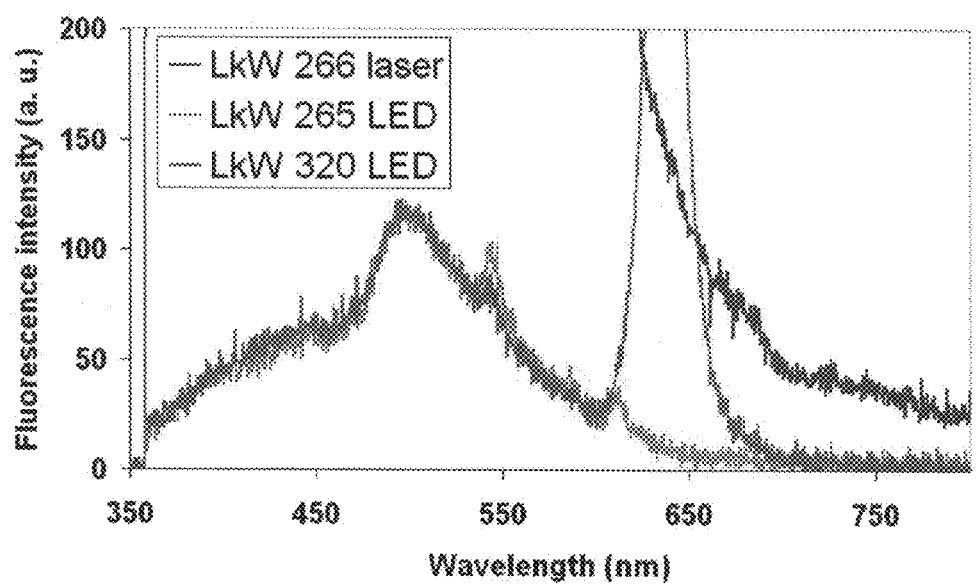
FIG. 18 is a graphical depiction of LED and laser fluorescence of pond water (without use of optical filters)
Figure 19:
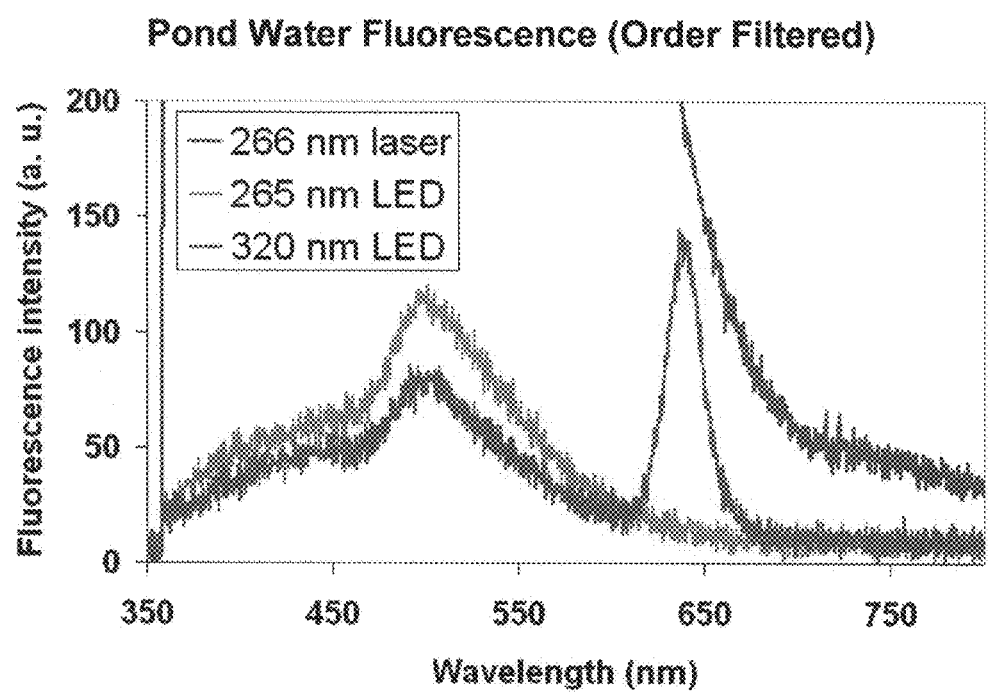
FIG. 19 is a graphical depiction of LED and laser fluorescence of pond water (with use of optical filters)

FIGS. 16 and 17 depict LED detection of DOCs in tap water, and FIGS. 18 and 19 depict detection of pond water samples.

Figure 20:
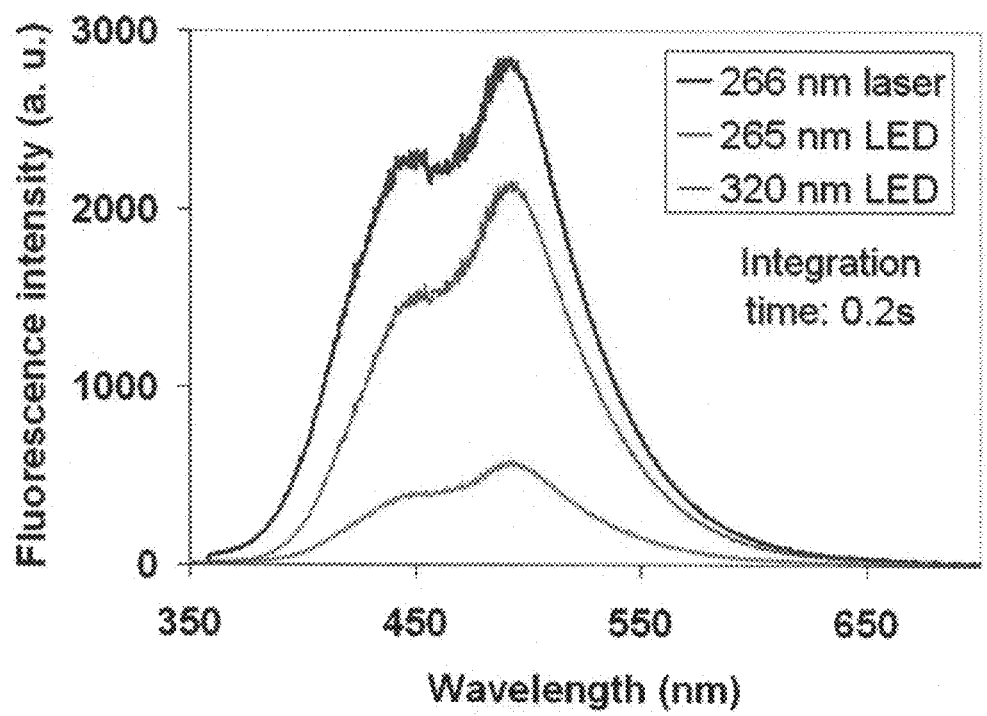
FIG. 20 is a graphical depiction of LED and laser fluorescence of tonic (quinine) water used as a fluorescence standard.

FIG. 20 depicts the fluorescence spectrum measured for tonic (quinine) water which can be used as a fluorescence standard for LIF and related instruments.

What is claimed is:

1. A method for detecting trace levels of dissolved organic compounds and leached plastic compounds in a body of water, comprising the steps of:
providing a pulsating deep ultraviolet (UV) light-emitting diode;
operating said deep UV light-emitting diode at an excitation of about 265 nm;
selecting a focal volume in said body of water;
illuminating said focal volume in said body of water with light emitted by said deep UV light-emitting diode;
detecting fluorescence signals in a range of about 450 nm to 500 nm from dissolved organic compounds in said focal volume by illuminating water in said focal volume with said pulsating light-emitting diode and detecting fluorescence signals having a duration of about 50 ns with a boxcar integrator to provide gated noise rejection of said fluorescence signals, said gated noise rejection providing increased sensitivity;
reducing out-of-band light-emitting diode emissions and substantially eliminating second order optical interference signals by employing optical absorption filters and optical bandpass filters to improve detection of said fluorescent signals in said range.

2. The method of claim 1, further comprising the step of:
detecting said fluorescence signals at an emission of about 310 nm from leached plastic compounds in said focal volume.

3. The method of claim 1, further comprising the steps of:
employing a continuous wave light-emitting diode excitation source with detection sensitivity within a factor of twenty (20) to thirty (30) times less than the detection sensitivity of a pulsed (8.6 KHz) 266 nm laser source that is operated at 8.6 KHz.

4. The method of claim 1, further comprising the steps of:
illuminating water in said focal volume with continuous wave light-emitting diodes and amplifying said fluorescence signals and illuminating said water in said focal volume with pulsed light-emitting diodes using gated boxcar integrators to optimize detection of optical emissions generated by contaminates in said water when said focal volume is so illuminated.

5. The method of claim 1, further comprising the steps of:
detecting said fluorescence emission by employing grating spectrometers and silicon detectors arrays in a sequential wheel arrangement with optical detectors.

6. The method of claim 1, further comprising the steps of producing similar fluorescence spectra by illuminating said focal volume with UV LED sources near 320 nm and reducing Mie and Rayleigh scatter and second order grating interference by employing optical blocking filters.

7. The method of claim 1, further comprising the steps of the operating said deep-UV light emitting diodes at an excitation of wavelengths near 200 nm to 260 nm to reduce a need for spectral optical filters near the shorter wavelengths and to separate second order scatter interferences from the DOC fluorescence spectral emission near 450 nm to 500 nm.

8. The method of claim 1, further comprising the steps of routing the LED excitation beam to a focal volume within a quartz cell employing a light-guiding means and collecting the fluorescence emission emitted from the excited focal volume.

9. The method of claim 8, further comprising the step of providing said light-guiding mean in the form of a lens.

10. The method of claim 8, further comprising the step of providing said light-guiding means in the form of fiber optics.

11. The method of claim 8, further comprising the steps of routing the LED excitation beam to a focal volume within a water container by employing a light-guiding means and collecting the fluorescence emission emitted from the excited focal volume.

12. The method of claim 8, further comprising the steps of routing the LED excitation beam to a focal volume within a flowing stream of water by employing a light-guiding means and collecting the fluorescence emission emitted from the excited focal volume.

* * * * *